(12) United States Patent
Sjoede et al.

(10) Patent No.: US 10,648,008 B2
(45) Date of Patent: May 12, 2020

(54) LIGNOCELLULOSIC BIOMASS CONVERSION

(75) Inventors: Anders Sjoede, Sarpsborg (NO);
Anders Froelander, Sarpsborg (NO);
Martin Lersch, Sarpsborg (NO);
Gudbrand Roedsrud, Sarpsborg (NO)

(73) Assignee: Borregaard Industries, Limited, Norge, Sarpsborg (NO)

( * ) Notice: Subject to any disclaimer, the term of this patent is extended or adjusted under 35 U.S.C. 154(b) by 768 days.

(21) Appl. No.: 13/140,488

(22) PCT Filed: Dec. 16, 2009

(86) PCT No.: PCT/EP2009/009046
§ 371 (c)(1),
(2), (4) Date: Jun. 17, 2011

(87) PCT Pub. No.: WO2010/078930
PCT Pub. Date: Jul. 15, 2010

(65) Prior Publication Data
US 2011/0250638 A1   Oct. 13, 2011

Related U.S. Application Data

(60) Provisional application No. 61/138,378, filed on Dec. 17, 2008.

(30) Foreign Application Priority Data

Dec. 17, 2008 (EP) .................... 08021952
Oct. 22, 2009 (EP) .................... 09013355

(51) Int. Cl.
| C12P 21/00 | (2006.01) |
| C12P 19/02 | (2006.01) |
| C12P 19/14 | (2006.01) |
| C12P 7/10 | (2006.01) |
| D21C 1/06 | (2006.01) |
| D21C 1/04 | (2006.01) |
| D21C 3/06 | (2006.01) |

(52) U.S. Cl.
CPC ............ *C12P 19/02* (2013.01); *C12P 7/10* (2013.01); *C12P 19/14* (2013.01); *D21C 1/04* (2013.01); *D21C 1/06* (2013.01); *D21C 3/06* (2013.01); *C12P 2201/00* (2013.01); *Y02E 50/16* (2013.01); *Y02P 20/582* (2015.11)

(58) Field of Classification Search
None
See application file for complete search history.

(56) References Cited

U.S. PATENT DOCUMENTS

| 2,734,836 A | 2/1956 | Elian et al. |
| 3,532,594 A | 10/1970 | Richter |
| 3,787,241 A | 1/1974 | Eickemeyer |
| 4,226,638 A | 10/1980 | Pfeiffer |
| 4,384,897 A | 5/1983 | Brink |
| 4,436,586 A | 3/1984 | Elmore |
| 4,511,433 A | 4/1985 | Tournier et al. |
| 4,564,595 A | 1/1986 | Neves |
| 4,612,286 A | 9/1986 | Sherman et al. |
| 4,615,742 A | 10/1986 | Wright |
| 4,634,499 A * | 1/1987 | Ampulski ............. 162/84 |
| 4,668,340 A | 5/1987 | Sherman |
| 4,995,943 A | 2/1991 | Rehberg |
| 5,043,433 A | 8/1991 | Dilling |
| 5,125,977 A | 6/1992 | Grohmann et al. |
| 5,221,357 A | 6/1993 | Brink |
| 5,424,417 A * | 6/1995 | Torget et al. ............. 536/56 |
| 6,423,145 B1 | 7/2002 | Nguyen et al. |
| 9,193,982 B2 | 11/2015 | Sjoede et al. |
| 2008/0190013 A1 | 8/2008 | Argyropoulos |
| 2009/0298149 A1 | 12/2009 | Wang et al. |

FOREIGN PATENT DOCUMENTS

| BR | 9706078 | 7/1999 |
| CN | 101381754 | 3/2009 |
| JP | 2008/092910 A | 4/2008 |
| SE | 527646 C2 | 3/2006 |
| SE | 527646 | 5/2006 |
| WO | WO 2006128304 | 12/2006 |

OTHER PUBLICATIONS

Biermann et al. "The Handbook of Pulping and Papermaking" 2nd Ed. 1996, 31 pgs.*
Krotschek "Pulping Technology and Equiptment" from Handbook of Pulp, Edited by Sixta, 1996, 174 pgs.*
Lawford et al. "Production of Ethanol from Pulp Mill Hardwood and Softwood Spent Sulfite Liquors by Genetically Engineered *E. coli*" Applied Biochemistry and Biotechnology, vol. 39/40, 1993, pp. 667-685.*
Shallom et al. "Microbial hemicellulases" Current Opinion in Microbiology 2003, 6:219-228.*
Pan et al. "Enhanced Enzymatic Hydrolysis of Steam-Exploded Douglas Fir Wood by Alkali-Oxygen Post-treatment" Applied Biochemistry and Biotechnology, vol. 113-116, 2004, pp. 1103-1114.*

(Continued)

*Primary Examiner* — Thane Underdahl
(74) *Attorney, Agent, or Firm* — William R. Haulbrook; Peter A. Flynn; Choate, Hall & Stewart LLP

(57) ABSTRACT

The present invention relates to a process for the production of second generation biofuels and/or sugar based chemicals—for example ethanol, butanol etc—and/or materials—for example plastics, single cell proteins etc.—together with sulfonated lignin from lignocellulosic biomass, in particular from lignocellulosic biomass comprising, among others, annual plants, agricultural waste, or wood. In particular, the present invention relates to a process for the production of sugar based chemicals, biofuels or materials together with sulfonated lignin from lignocellulosic biomass comprising the pretreatment of a lignocellulosic biomass in a sulfite cooking step.

17 Claims, 4 Drawing Sheets

(56) References Cited

OTHER PUBLICATIONS

Perkins (Chair): "AIChE—The 2008 Annual Meeting, Philadelphia, USA/Topical 4: Sustainable biorefineries (T4)", Google Nov. 19, 2008.
Zhu: AIChE—The 2008 Annual Meeting, Philadelphia, USA/Sporl for robust enzymatic hydrolysis of woody biomass:, Google Nov. 19, 2008.
Deverell: "Ethanol production from wood hydrolysates using Pachysolen Tannophilus", Biotechnology Letters, vol. 5, 1983, pp. 475-480.
Hendriks, et al.: "Pretreatments to enhance the digestibility of lignocellulosic biomass", Bioresource Technology, vol. 100, Jul. 2, 2008, pp. 10-18.
Sjode, et al: "The potential in bioethanol production from waste fiber sludges in pulp mill-based biorefineries", Applied Biochemistry and Biotechnology, vol. 136-140, 2007, pp. 327-338.
Sims, et al: "From $1^{st}$—to $2^{nd}$-generation biofuel technologies", 2007 International Energy Agency.
Assarsson, et al.: "Utvecklingsmojlighter inom biokombinatet I Alfredshem", 2005 Processum Technology Park, Ornskoldsvik, Sweden.
Kuhad et al.: "Hydrolytic potential of extracellular enzymes from a mutant strain of Fusarium oxysporum", Bioprocess Engineering, vol. 20, 1999, pp. 133-135.
Bjorling, et al.: "Evaluation of xylose-fermenting yeasts for ethanol production from spent sulfite liquor", Enzyme and Microbial Technology, vol. 11, 1989, pp. 240-246.
Zhu, et al.: "Sulfite pretreatment (SPORL) for robust enzymatic saccharification of spruce and red pine", Bioresource Technology, vol. 100, Dec. 31, 2008, pp. 2411-2418.
Wang, et al.: "Sulfite pretreatment to overcome recalcitrance of lignocellulose (SPORL) for robust enzymatic saccharification of hardwoods", Biotechnology Progress, vol. 25, Jun. 23, 2009, pp. 1086-1093.
Database WPI Thomson Scientific, London, GB; AN 2009-G46615, "Preparing fermentable sugar, involves adding cellulose material to aqueous solution of sulfite and alkali compound, dehydrating cellulose product insoluble in sulfonated reaction solution and hydrolyzing product in cellulose enzyme".
Mooney, et al.: "The effect of initial pore volume and lignin content on the enzymatic hydrolysis of softwoods", Bioresource Technology, vol. 64, Issue 2, May 2, 1998, pp. 113-119.
Lu, et al.: "Cellulase Adsorption and an Evaluation of Enzyme Recycle During Hydrolysis of Steam-Exploded Softwood Residues", Applied Biochemistry and Biotechnology, vols. 98-100, 2002, pp. 641-654.
International Search Report for PCT/EP2009/009046 published Jan. 27, 2011, 6 pgs.
Zhu, J.Y., et al., "Specific surface to evaluate the efficiencies of milling and pretreatment of wood for enzymatic saccharification", Chemical Engineering Science, 64, 474-485 (2009).
Zhau,X, et al, "Acceleration of ethanol production from paper mill waste fiber by supplementation with β-glucosidase", Enzyme Microb. Technol., 15, 62-65 (1993).
Moritz. J., et al., "Ethanol Production from Spent Sulfite Liquor Fortified by Hydrolysis of Pulp Mill Primary Clarifier Sludge", Applied Biochemistry and Biotechnology, 57/58, 689-698 (1996).
Moritz, J. Thesis "Ethanol Production From Waste Biomass: Enzymatic Hydrolysis and Fermentation of Sulphite Pulp Mill Primary Clarifier Sludge", The University of British Columbia, (1996), 10 pgs.
Magdzinski, L., "Tembec Temiscaming integrated biorefinery", Pulp & Paper Canada, 107:6, 44-46 (2006).
Assarsson, A., "Development opportunities within Biokombinatet in Alfredshem: A vision document Processum Technology Park" The European Union, Report No. 1, p. 1-18, (2005) (translated).
Assarsson, A., "Development opportunities within Biokombinatet in Alfredshem: A vision document Processum Technology Park" The European Union, Report No. 1, p. 15-16, (2005) (translated).
Translation of Chinese Office Action for 200980151250.2, dated Jan. 25, 2013 (8 pages).
Alvira, P. et al., Pretreatment technologies for an efficient bioethanol production process based on enzymatic hydrolysis: A review, Bioresource Technology, 101:4851-4861 (2010).
Production of Enzyme for Saccharification from Alkaline Treated Woody Biomass, J. Jpn. Inst. Energy, 87(1):68-71 (2008).
Shuai, L. et al., Comparative study of SPORL and dilute-acid pretreatments of spruce for cellulosic ethanol production, Bioresource Technology, 101:3106-3114 (2010).
Toven, K. and Oyaas, K, Low temperature sulfonation of lignocellulose for effective biomass deconstruction and conversion, In: Presented at the Nordic Wood and Biorefinery Conference, Hensinki, Finland, 12 pages (2012).
Scott, A., Seeking a Home for Papermaking Waste, American Chemical Society, Chemical Engineering News, published on Mar. 30, 2015 in cen.acs.org.
Kumar, L. et al., Influence of Steam Pretreatment Severity on Post-Treatments Used to Enhance the Enzymatic Hydrolysis of Pretreated Softwoods at Low Enzyme Loadings, Biotechnology and Engineering, 1-12 (2011).

\* cited by examiner

LIGNOCELLULOSIC BIOMASS CONVERSION

CROSS-REFERENCE TO RELATED APPLICATIONS

This application is a National Phase application under 35 U.S.C. § 371 of International Application PCT/EP2009/009046, filed Dec. 16, 2009, which claims priority to EP 08021952.0, filed Dec. 18, 2008, U.S. provisional application Ser. No. 61/138,378, filed Dec. 17, 2008, and EP 09013355.4, filed Oct. 22, 2009, the entirety of each of which is hereby incorporated herein by reference.

The present invention relates to a process for the production of second generation biofuels and/or sugar based chemicals—for example ethanol, butanol etc.—and/or materials—for example plastics, single cell proteins etc.—together with sulfonated lignin (lignosulfonate) from lignocellulosic biomass, in particular from lignocellulosic biomass comprising, among others, energy crops, annual plants, agricultural waste or wood.

In particular, the present invention relates to a process for the production of monosaccharides, sugar based chemicals, biofuels or materials together with sulfonated lignin from lignocellulosic biomass comprising at least the following steps:
(i) pretreatment of a lignocellulosic biomass in a sulfite cooking step;
(ii) separation of the pretreated lignocellulosic biomass from step (i) into
    (a) a liquid "spent sulfite liquor" phase comprising 50% or more of the lignin of the lignocellulosic biomass in the form of sulfonated lignin, and into
    (b) a pulp comprising 70% or more of the cellulose of the lignocellulosic biomass;
(iii) hydrolysis of the pulp (b) from step (ii) into a sugar chemistry platform comprising monosaccharides;
(iv) optionally further processing of the monosaccharides from step (iii) resulting in useful chemicals, biofuels and/or proteins; and
(v) direct conversion or further processing of the sulfonated lignin of the liquid phase (a) from step (ii) into useful chemicals and/or materials.

BACKGROUND AND PRIOR ART

As is generally accepted, the resources for petroleum-based chemicals and for petroleum used as (fossil) fuel are limited. One presently used alternative resource is "biofuel" as obtained from biomass. Various sources of biomass may be used.

"First-generation biofuels" are biofuels made from sugar, starch, vegetable oil, or animal fats using conventional technology. Exemplary basic feedstocks for the production of first generation biofuels are seeds or grains such as wheat, which yield starch that is hydrolyzed and fermented into bioethanol, or sunflower seeds, which are pressed to yield vegetable oil that can be transformed into biodiesel. However, these feedstocks could instead enter the animal or human food chain. Therefore, first generation biofuels have been criticised for diverting food away from the human food chain, leading to food shortages and price increases.

By contrast, "second generation biofuel" can be produced sustainably by using biomass comprised of the residual non-food (i.e. non digestible) parts of current crops, such as stems, leaves, bagasse (sugarcane fiber residue), husks etc. that are left behind once the food crop has been extracted, as well as other feedstock that is not used for food purposes (non food crops), such as wood, annual plants and cereals that comprise little grain, and also industry waste such as sawdust, skins and pulp from fruit pressing, wine processing etc.

One common problem in producing second generation biofuels from biomass is the extraction of fermentable feedstock from the "woody" or fibrous biomass. In particular, the carbohydrates that can be hydrolyzed and fermented (in particular cellulose and, if present, hemicellulose) are intertwined with lignin (hence, in the following, such biomass will be referred to as lignocellulosic biomass').

Lignin is a complex heterogeneous polymer that cannot be subjected to the hydrolysis/fermentation cycle applied to the cellulose/hemicellulose. Lignin as commonly produced is not a particularly useful substance and is typically discarded or burned (generating some benefit as process heat) after separation. In a future efficient biorefinery, all major components of lignocellulose not only need to be separated but also all have to be utilized. The carbohydrates may be used as a platform for sugar based chemicals, e.g. ethanol.

Pretreatment (before hydrolysis) of the lignocellulosic material is conventionally achieved by means of steam heating, steam explosion or enzymatic pretreatment, among others.

A continuous process for treating a lignocellulosic feedstock is provided in WO 2006/128304. This method comprises pretreating the lignocellulosic feedstock under pressure in a pretreatment reactor at a pH between about 0.4 and about 2.0. A minor part of the lignin will be dissolved under acidic conditions like this, but the majority of the biomass lignin fraction from this process will not be soluble in water, and will be separated together with other insolubles.

Another method of converting lignocellulosic material is described in U.S. Pat. No. 6,423,145. A modified dilute acid method of hydrolyzing the cellulose and hemicellulose in lignocellulosic material under conditions to obtain higher overall fermentable sugar yields than is obtainable using dilute acid alone, comprising: impregnating a lignocellulosic feedstock with a mixture of an amount of aqueous solution of a dilute acid catalyst and a metal salt catalyst sufficient to provide higher overall fermentable sugar yields than is obtainable when hydrolyzing with dilute acid alone; loading the impregnated lignocellulosic feed-stock into a reactor and heating for a sufficient period of time to hydrolyze substantially all of the hemicellulose and greater than 45% of the cellulose to water soluble sugars; and recovering the water soluble sugars. This process produces insoluble lignins that can be separated together with non-hydrolysed biomass and other insolubles.

A more recent method of pretreatment is described in US 2008/0190013. US '013 disclosed a method for converting lignocellulosic material into biofuel. In particular embodiments, the method comprises pre-treating lignocellulosic material by dissolving the material in ionic liquids. The pretreated lignocellulosic material can be isolated, such as by precipitation with a regenerating solvent (e.g., water), and be used directly in the formation of biofuel, including undergoing hydrolysis to form sugar and fermentation to form fuel, such as bioethanol. The ionic liquid can be recycled for further use, such as by evaporation of the water introduced during precipitation, and the recycling provides a route to a hemicellulose rich fraction and an ionic liquid of consistent quality and wood dissolution characteristics. The recovered hemicelluloses are of significant utilization potential toward commodity and specialty applications. This process also produces lignins insoluble in water.

Swedish Patent no. 527 646 proposes a process for the production of fuels for engines and fuel cells from lignocellulosic material. The lignin is dissolved from the lignocellulosic material by a cook, preferably by a soda cook. The cooking liquor is gasified to produce syngas and subsequently methanol, DME etc., while the cellulose and the hemicellulose in the pulp are hydrolysed by acid (weak or strong) or enzymes and then fermented to ethanol.

An article by J. Y. Zhu et al. ("Sulfite Pretreatment (SPORL) for robust enzymatic saccharification of spruce and red pine"; Bioresource Technology 100 (2009) 2411-2418) published online on Dec. 31, 2008 reports sulfite pretreatment to overcome recalcitrance of lignocellulose for the efficient bioconversion of softwoods.

In order to arrive at a process where the conversion of second generation biomass to biofuels is performed in an economic and sustainable manner, a number of challenges need to be addressed.

The lignin component is usually burned, however it is desirable to be able to convert the lignin to valuable chemicals of commercial value. However, lignins from many of the processes are impure and are poorly soluble in water which makes them hard to process further into valuable chemicals.

The lignins in biomass are known to adsorb cellulytic enzymes and thereby having an inhibiting effect on the enzymes used to hydrolyse cellulose to cellobiose and glucose. This substantially increases the amounts of enzymes needed. In addition, the complexity of the enzyme mixture needed is substantial since the cellulose fibers still are embedded in both lignin and hemicellulose. Cost of enzymes therefore is a major challenge in biomass to biofuel processes in addition to low total yield of products. Unfortunately, all known pretreatment processes leave lignins that are inhibiting these enzymes, even when reduced to low levels (below 5%).

Recycling of enzymes is also difficult since the enzymes are unspecifically bound to the lignin in the hydrolysis process step.

Another challenge of second generation bioethanol production from a commercial point of view is the low overall yield of valuable chemicals and in particular to provide valuable chemicals of a higher value than the energy value from xylan and lignin.

In light of the prior art, a process for converting lignocellulosic biomass is sought that better prepares the cellulose for hydrolysis as well as allows for a more complete use of the biomass in providing a higher yield in performance chemicals and/or biofuel.

These objects and others are solved by a process for the production of monosaccharides, sugar based chemicals or biofuels or materials together with sulfonated lignin from lignocellulosic biomass comprising at least the following steps:
(i) pretreatment of a lignocellulosic biomass in a sulfite cooking step;
(ii) separation of the pretreated lignocellulosic biomass from step (i) into
   (a) a liquid "spent sulfite liquor" phase comprising 50% or more of the lignin of the lignocellulosic biomass in the form of sulfonated lignin, and into
   (b) a pulp comprising 70% or more of the cellulose of the lignocellulosic biomass;
(iii) hydrolysis of the pulp (b) from step (ii) into a sugar chemistry platform comprising monosaccharides;
(iv) optionally further processing of the monosaccharides from step (iii) resulting in useful chemicals, biofuels and/or proteins; and
(v) direct conversion or further processing of the sulfonated lignin of the liquid phase (a) from step (ii) into useful chemicals and/or materials.

In a preferred embodiment and based on the type of raw lignocellulosic biomass, a mechanical treatment step (0) may be performed prior to step (i). In said mechanical treatment step, the biomass is divided into smaller pieces or particles by mechanical treatment. This step is obsolete, for example, in case of using bagasse as a raw material.

In the pretreatment step (i), the lignocellulosic biomass is cooked with a sulfite, preferably a sodium, calcium, ammonium or magnesium sulfite under acidic, neutral or basic conditions. This pretreatment step dissolves most of the lignin as lignosulfonate together with parts of the hemicellulose. This dissolved or liquid phase (pulping liquor; also known as "Spent Sulfite Liquor", "SSL") is the liquid SSL phase (a) of step (ii). The cellulose is left almost intact in the pulp (b) together with parts of the hemicellulose.

By treating the lignocellulosic biomass according to the process described above, a particularly efficient biorefinery platform is generated.

By specifically employing a sulfite cook as the pretreatment step in the overall process, a good separation of the carbohydrates cellulose and hemicellulose from the lignin is achieved. The resulting pulp is particularly easy to hydrolyze due to the modification during the cook, leading to reduced cost of saccharification.

The content of the residual, non-solubilized lignin in the pulp which is remaining after the inventive treatment is found to be of no significant importance for how easily the cellulose can be hydrolyzed by enzymes. This is highly surprising and different from what has been reported earlier, see Mooney C. A. et al., 1998, "The effect of the initial pore volume and lignin content on the enzymatic hydrolysis of softwood", Biores. Technol. 64, 2, 113-119 and Lu Y. et al., 2002, "Cellulase adsorption and an evaluation of enzyme recycle during hydrolysis of steam-exploded softwood residues", Appl. Biochem. Biotechnol. 98-100, 641-654.

Without wishing to be bound by theory, one may assume that the sulfite pretreatment alters the lignin in a way that reduces or removes its inhibitory effect and thereby makes high hydrolysis yield at a low enzyme consumption possible.

This non-inhibitory property of the residual lignin also makes it easier to recirculate the enzymes by e.g. substrate adsorption or membrane filtration and makes the use of long-living enzymes more interesting and the overall process more economical.

Furthermore, a much higher yield of marketable products is reached compared to other processes, mainly due to the isolation and utilization of a marketable lignin product, namely lignosulfonate.

By practicing the process according to the invention, more than 80% by weight of the lignocellulosic biomass feedstock can be transformed into marketable products and yields of up to 90% of the theoretical amount of fermentable sugars are obtainable. One embodiment of the integrated overall process is shown exemplarly in FIG. 1 and is described in more detail below.

Hence, the main benefits of the present process comprise:
Lignin is converted from an insoluble form to a water soluble form that facilitates easy separation of water soluble lignins with surprisingly superior properties as performance chemicals and in the production of pure lignin chemicals.

Furthermore, the cellulose in the pulp is easily degraded by enzymes as explained above and brings the enzyme consumption and costs to an acceptable level. This is believed to be due to the fact that during the sulfite cook step, the cellulose fibers are separated and not longer embedded in lignin and hemicelluloses. Also, the lignin left in the cellulose containing pulp after the sulfite pretreatment is less inhibitory to the enzymes than native lignin in the downstream processing step of enzymatic hydrolysis. This effect was completely unexpected.

Since enzymes apparently are not adsorbed irreversibly to the lignin left in the cellulose pulp exposed to the hydrolysis step, the enzymes may also be recycled. This additionally reduces the enzyme consumption and thereby the process costs.

DETAILED DESCRIPTION OF THE PRESENT INVENTION

Raw Materials

Figure 1:
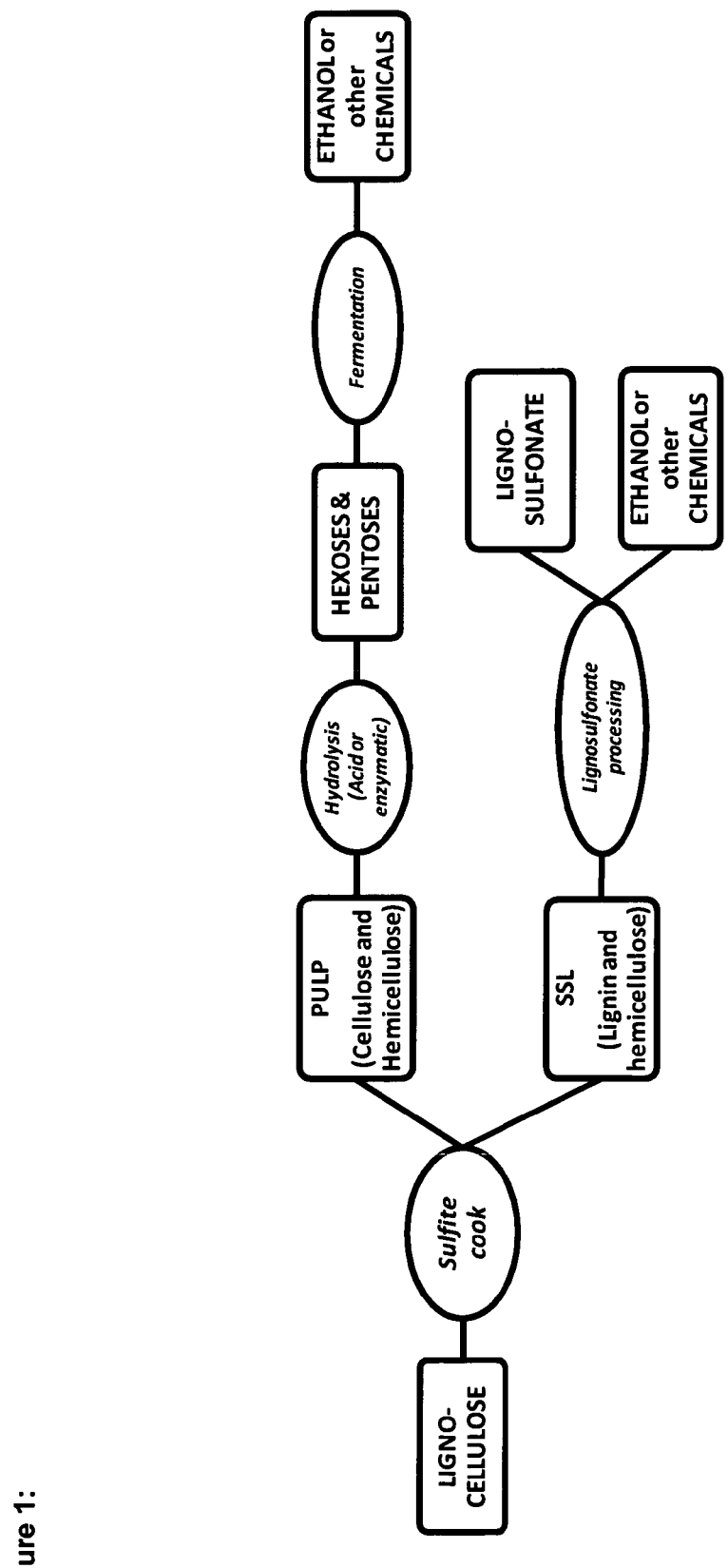
FIG. 1 is a flow sheet of a preferred biorefinery concept in accordance with the present invention.
Figure 2:
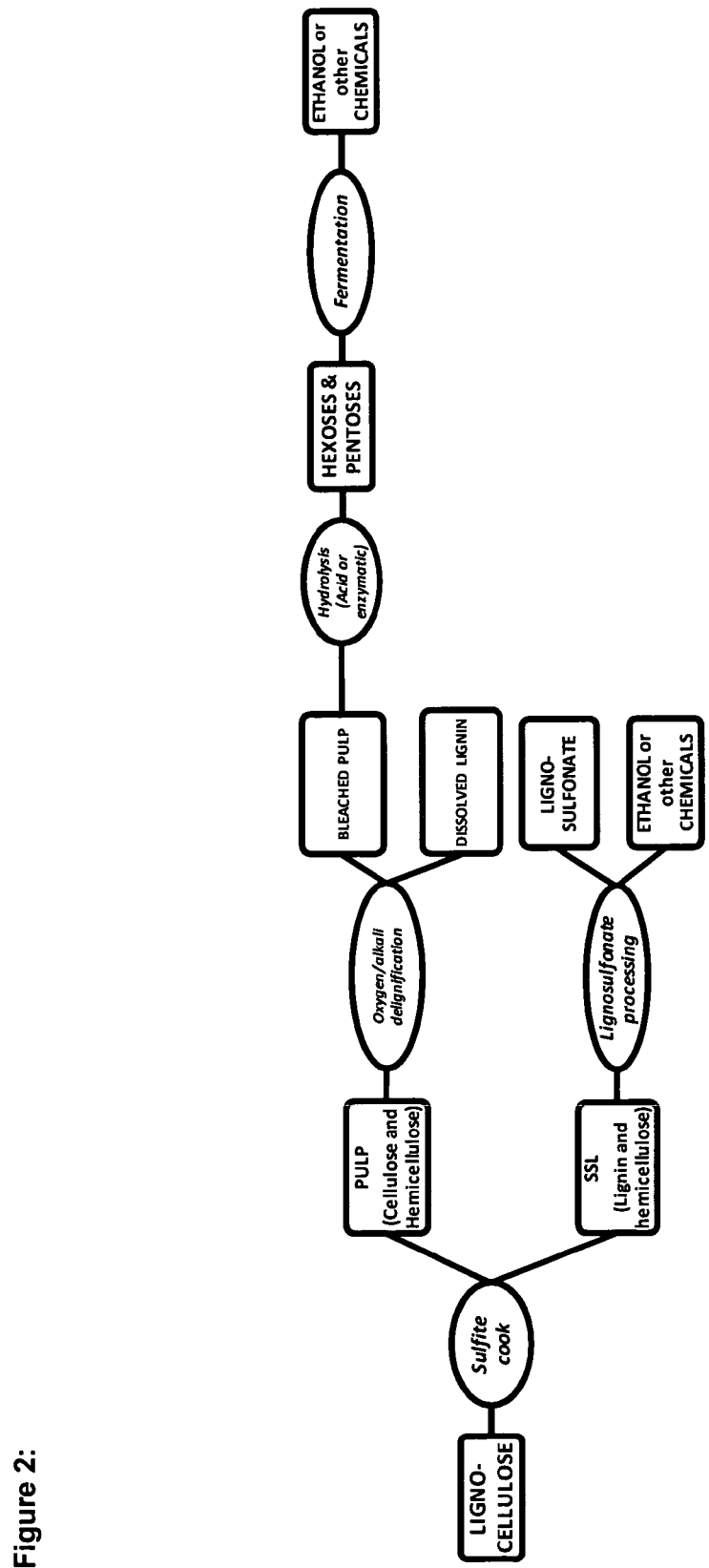
FIG. 2 is a flow sheet of a preferred embodiment additionally using oxygen and/or alkali delignification.

In respect to the raw material for the lignocellulosic biomass, no principal limitations exist, except that the biomass must comprise cellulose and lignin. Preferred raw materials that are suited for the present biorefinery concept are energy crops, annual plants, agricultural residues and wood.

Commercial energy crops are typically densely planted, high yielding crop species that are preferably of no or of limited value as foods. For example, wooden crops such as Salix, Miscanthus, Willow or Poplar are preferred energy crops.

Preferred examples of annual plants are straw, sugarcane and cassava. They all grow fast and generally have a relatively low amount of lignin (compared to wood).

Agricultural residues include those parts of arable crops not to be used for the primary purpose of producing food, feed or fibers, for example used animal bedding and feathers. These residues are exemplified by bagasse from sugarcane and corn stalk.

The particularly preferred starting material of sugarcane can be divided in bagasse, sugar and straw. Bagasse is a fibrous material consisting of cellulose, hemicellulose, lignin, extractives, inorganic salts and other organic substances such as proteins and organic acids.

Bagasse and hardwood have many similarities, i.e. high xylan content, shorter fiber length and lower lignin and cellulose content compared to softwood. However bagasse has a slightly higher ash content. The ash content may be explained by differences in plant morphology and harvesting method. The short fiber length in bagasse is mainly due to its high pith content (~30%).

Overall, based on the fact that no mechanical size reduction may be needed and that higher hydrolysis yields are obtained, it is particularly preferred to conduct the process according to the present invention with non-wood agricultural residues, in particular bagasse, as raw materials.

Wood is also a material for the present biorefinery concept. Therein, all types of wood are suitable.

The lignocellulosic biomass is (pre)treated prior to hydrolyis and further processing of the monosaccharides and other components. A (pre)treatment may be mechanical or chemical.

In mechanical (pre)treatment, momentum or energy is transferred into the raw material, for example by means of dividing or cutting or beating biomass into smaller particles. Therein, no chemical reagents are added and the chemical structure of the components of the raw material remains essentially unaffected.

In chemical (pre)treatment, at least one chemical reagent is added and the chemical structure of at least one component of the raw material is altered. As will be discussed in more detail below, "sulfite pulping" is a chemical pretreatment.

Mechanical Treatment

Based on the type of raw lignocellulosic biomass, a mechanical treatment step (0) may be performed prior to step (i). In said mechanical treatment step, the biomass is divided into smaller pieces or particles by mechanical treatment. This step is obsolete, for example, in case bagasse or sawdust is used as a raw material.

Therefore, in a preferred embodiment, a raw material is used in the lignocellulosic biomass conversion that does not require mechanical (pre)treatment and wherein sulfite cooking is the only (pre)treatment.

Pretreatment: Sulfite Pulping

Pulping (or cooking) wood with sulfite was one of the first chemical methods used in wood pulping as early as in the 1860s.

The first pulp mill using the sulfite process was built in Sweden in 1874 and used magnesium as the counter ion. Calcium became the standard counter ion until the 1950s. Sulfite pulping was the dominant process for making wood pulp until it was sur-passed by the so-called "Kraft" process in the 1940s. The predominance of Kraft-pulping is based on the fact that the sulfite process is typically performed under conditions that hydrolyze some of the cellulose, which means that sulfite pulp fibers are not as strong as Kraft pulp fibers, which is a particular disadvantage of sulfite pulping for the predominant application of paper pulping. Sulfite pulps now account for less than 10% of the total chemical pulp production. These remaining sulfite pulps are used for specialty paper applications and (for example in the form of so-called "dissolving pulp") for making cellulose derivatives.

Unlike the sodium based Kraft process that is performed at a pH of the fresh cooking liquor of about 13, the sulfite process is characterized in that it covers the whole pH range. The pH may range from <1 (using sulfur dioxide solutions in water) to >13 (using sulfur dioxide or sodium sulfite or sodium bisulfite together with sodium hydroxide).

Sulfite cooking may be divided into four main groups: acid, acid bisulfite, weak alkaline and alkaline sulfite pulping.

Another particular advantage of sulfite pretreatment relates to the lignin that is of particular interest in the framework of the present invention.

In its natural state lignin is insoluble in water and hydrophobic. When reacted with sulfite, lignin is converted to sulfonated lignin (lignosulfonates) that has drastically different properties than lignin. The introduction of sulfonic acid groups in lignin changes the polymer from a neutral to an anionically inactive compound to one of the strongest organic acids known, with a dissociation constant of 0.3. As opposed to naturally occuring lignin, sulfonated lignin as such are useful performance chemicals or can be converted into commercially viable chemicals/materials. The lignin conversion of the present process is not achieved in any other of the known pretreatment processes, in particular not in the pretreatment processes known in the context of biomass conversion. The present process therefore allows for producing valuable performance chemicals (sulfonated lignin) from lignocellulosic biomass and in particular from non-wood-based biomass, e.g. stems, bagasse or annual plants.

In the pretreatment step (i) of the present invention, the lignocellulosic biomass is cooked with a sulfite, preferably a sodium, calcium, ammonium or magnesium sulfite under acidic, neutral or basic conditions. This pretreatment step dissolves most of the lignin as sulfonated lignin (lignosulfonate) together with parts of the hemicellulose. This dissolved or liquid phase (pulping liquor) is the liquid SSL phase (a) of step (ii). The cellulose is left almost intact in the pulp (b) together with parts of the hemicellulose.

The use of sulfite cooking as a pre-treatment step in the production of fuels or chemicals from fermentable sugars is very efficient as it leads to higher overall yields of chemicals. In essence, a higher output (>80%) of useful chemicals is achieved than in any other known sugar-platform biorefinery technology.

In particular, lower costs for the hydrolysis are achieved based on a pre-treatment that separates cellulose efficiently from the other constituents, in particular lignin, in one step.

The fact that the cellulose pulp resulting from the one-step pretreatment is particularly low in impurities, in particular lignin, makes it easier to develop or adapt enzymes for the hydrolysis.

Also, the sulfite pretreatment step of the present invention allows for increased flexibility in managing the process (pH from 1 to 13) and in terms of in which phase the hemicellulose ends up (i.e. whether the hemicellulose is predominantly in the liquid SSL phase or predominantly in the cellulose pulp). The sulfite pretreatment step also results in increased flexibility in terms of in what form (monomeric/polymeric) the hemicellulose ends up.

The sulfite pretreatment according to the present invention may be performed according to one of the following preferred embodiments. Therein and throughout the present disclosure, the "sulfite pretreatment" is also referred to as "cook":

- acidic cook (preferably $SO_2$ with a hydroxide, further preferably with $Ca(OH)_2$, NaOH, $NH_4OH$ or $Mg(OH)_2$),
- bisulfite cook (preferably $SO_2$ with a hydroxide, further preferably with NaOH, $NH_4OH$ or $Mg(OH)_2$),
- weak alkaline cook (preferably $Na_2SO_3$, further preferably with $Na_2CO_3$) and
- alkaline cook (preferably $Na_2SO_3$ with a hydroxide, further preferably with NaOH).

A correlation exists between the pH employed during the cook and the Kappa number of the produced pulp, in particular high pH-values lead to low Kappa numbers. The Kappa number is an indication of the lignin content or bleachability of the pulp. The Kappa number relates to the lignin content of the pulp and can be used to monitor the effectiveness of the lignin-extraction phase of the pulping process. The number is typically in the range of 1 to 100 for a pulp and is established by measuring the amount of a standard potassium permanganate solution that is consumed by the pulp being considered. Details on how the Kappa number is determined are given in ISO 302:2004.

For each type of cook, the impact of several cooking variables such as temperature, time, liquid to solid ratio and amount of cooking chemicals can be used to affect the composition and properties of the pulp, in particular lignin content and hemicellulose content in the pulp phase and in the liquid SSL phase, respectively (see FIG. 1: "Pulp"-phase and "SSL" liquid SSL phase).

Acid cooks result in pulps with a relatively high residual lignin content (15-40%) in the pulp phase (Kappa numbers 50-100). Acid sulfite cooks furthermore result in sulfonated lignins having a high degree of sulfonation. The molecular weight of the sulfonated lignin is also higher compared with alkaline sulfite cooks. During acid sulfite cooking, the polysaccharides are partly degraded, mainly by hydrolysis of the glycosidic bonds. The hemicellulose is more sensitive to hydrolysis than the cellulose. However, as opposed to paper-making, this partial hydrolysis of (hemi)cellulose could be advantageous in a biorefinery where the (hemi)cellulose potentially needs to be hydrolyzed and broken down anyway.

A large part (70% or more) of the hemicellulose (mainly present as xylan) is hydrolyzed to monosaccharides, mainly to xylose, during the cook and is dissolved in the cooking liquor, i.e. in the liquid SSL phase.

Therefore, according to a preferred embodiment of the present invention, an acid cook is performed as the pretreatment step (i), wherein 70% or more of the overall hemicellulose from the lignocellulosic biomass is hydrolyzed to xylose in step (i) and is present in the liquid SSL phase (b) in step (ii), i.e. the SSL that is separated from the cellulose pulp in step (ii).

In accordance with a preferred embodiment of the present invention, the sulfite pre-treatment step is an acid cook, further preferably an acid cook wherein the temperature is in the range from 125° C. to 160° C. Cooks at higher temperatures result in lower pulp yields and more extensive degradation of the monosaccharides in the SSLs. Therefore, it is preferred to keep the temperature of the acid cook at or below 160° C.

In accordance with a preferred embodiment of the present invention, the sulfite pre-treatment step is an acid cook and the cook is performed for a time interval of 60-300 minutes.

In accordance with a preferred embodiment of the present invention, the sulfite pre-treatment step is an acid cook and the liquid-to-solid ratio is from 3:1 to 10:1.

In accordance with a preferred embodiment of the present invention, the sulfite pre-treatment step is an acid cook and the amount of $SO_2$ is from 10 to 60% w/w, while the amount of base (hydroxide ion) is from 1 to 10% w/w, preferably from 2% to 7%. Unless indicated otherwise, "w/w" relates to "% weight" of the component in the working liquor to the weight of dry raw material.

In accordance with a preferred embodiment of the present invention, the sulfite pre-treatment step is an acid cook and the hydroxide employed is selected from the group consisting of NaOH, $Ca(OH)_2$, $Mg(OH)_2$, $NH_4OH$. Sodium cooks generally give lower Kappa numbers than calcium cooks.

Bisulfite cooks yield similar results as the acid cooks but generally lead to less carbohydrate degradation, higher SSL yields and, at temperatures above 150° C., lower Kappa numbers.

In bisulfite cooking, the xylan dissolved in the SSLs is hydrolyzed to xylose only to a smaller extent (less than 40%).

In regard to bisulfite cooks, the same preferred ranges apply for the temperature, the time interval and the liquid-to-solid ratio as disclosed above for acid cooks.

Alkaline and neutral pulps as discussed below in general are brighter and more easily dewatered than the acid and bisulfite pulps.

Alkaline cooks result in pulps with lower amounts of residual lignin (>80% of the lignin dissolved in the SSL phase, Kappa ~10) and higher xylan contents (<50% dissolved in the cooking liquor). The xylan dissolved in the SSLs is essentially not hydrolyzed to xylose.

Therefore, according to a preferred embodiment of the present invention, an alkaline cook is performed as the pretreatment step (i), wherein 80% or more of the overall lignin from the lignocellulosic biomass is present in the liquid SSL phase (b), i.e. the SSL that is separated from the cellulose pulp in step (ii). Increased alkali charges typically result in pulps with lower Kappa numbers.

In alkaline sulfite pulping, sodium hydroxide and sodium sulfite are preferably used as reagents. Alkaline sulfite pulping combines two strong delignification reagents, sulfite ions and hydroxide ions, thus resulting in an efficient delignification process. The sulfonated lignin from alkaline sulfite pulping will have a lower molecular weight and possibly be less sulfonated, due to reduced efficiency of the sulfite ion with increased pH and increased effect of the hydroxide ions. Hemicelluloses may be removed through dissolving, i.e. up to 50% of the xylan may be dissolved during an alkaline cook. However, if the pulp and cooking liquor are cooled before separation, the majority of the xylan is re-precipitated onto the pulp.

In accordance with a preferred embodiment of the present invention, the sulfite pre-treatment step is an alkaline cook, wherein, preferably, the temperature is in the range from 130° C. to 180° C., or preferably from 140° C. to 180° C.

In accordance with a preferred embodiment of the present invention, the sulfite pre-treatment step is an alkaline cook and the cook is performed for a time interval of 45 to 300 minutes.

In accordance with a preferred embodiment of the present invention, the sulfite pre-treatment step is an alkaline cook, further preferably an alkaline cook wherein the liquid-to-solid ratio is from 3:1 to 10:1.

In accordance with a preferred embodiment of the present invention, the sulfite pre-treatment step is an alkaline cook and the amount of $Na_2SO_3$ is from 5-60% w/w, while the amount of base is from 5 to 25% w/w.

In accordance with a preferred embodiment of the present invention, the sulfite pre-treatment step is an alkaline cook and the base employed is selected from the group consisting of NaOH or $NH_4OH$ ($NH_3$).

Adding anthraquinone to alkaline cooks improves the delignification and results in a higher degree of carbohydrates in the pulp. Therefore, if an alkaline cook is performed as the sulfite pretreatment step, the addition of anthraquinone to the cooking liquor is preferred.

Weak alkaline cooks give pulps similar to those of the alkaline cooks although with somewhat more residual lignin and xylan.

In the context of the present application, "weak alkaline sulfite cook" is defined as a cook with sodium sulfite and sodium carbonate. The main advantages of these cooks are the prevailing carbohydrate structures, i.e. both the cellulose and hemicellulose essentially remain in the pulp.

Adding anthraquinone to weak alkaline cooks improves the delignification and results in a higher degree of carbohydrates in the pulp. Therefore, if a weak alkaline cook is performed as the sulfite pretreatment step, the addition of anthraquinone to the cooking liquor is preferred.

In accordance with a preferred embodiment of the present invention, the sulfite pre-treatment step is a weak alkaline cook and the temperature is in the range from 140° C. to 180° C.

In accordance with a preferred embodiment of the present invention, the sulfite pre-treatment step is a weak alkaline cook and the cook is performed for a time interval of 45 to 300 minutes.

In accordance with a preferred embodiment of the present invention, the sulfite pre-treatment step is a weak alkaline cook and the liquid-to-solid ratio is from 3:1 to 10:1.

In accordance with a preferred embodiment of the present invention, the sulfite pre-treatment step is a weak alkaline cook and the amount of $Na_2SO_3$ is from 10 to 60% w/w, while the amount of $Na_2CO_3$ is from 3 to 25% w/w and preferably from 5 to 25% w/w.

The yield of cellulose and hemicellulose and the degree of delignification are considerably higher for high pH cooks (weak alkaline and alkaline) than for low pH cooks (acid and bisulfite). The high pH cooks give pulps of considerably higher viscosity than the low pH cooks.

Therefore, according to a preferred embodiment of the present invention, the pH value at which the sulfite cook of the pretreatment step (i) is performed, is higher than 5, preferably higher than 7, further preferably higher than 9.

Separation of Pulp and SSL

In step (ii) of the process according to the present invention, the pulp (solid phase; cellulose and hemicellulose) is separated from the Spent Sulfite Liquor (liquid SSL phase; SSL, sulfonated lignin and hemicellulose) by any separation method known to the person skilled in the art; in particular pressing, filtration, sedimentation or centrifugation.

In step (ii), the separation results in a liquid SSL phase. The organic part of the SSL predominantly comprises lignin (sulfonated lignin), i.e. comprises at least 50% of the lignin initially present in the lignocellulosic biomass, preferably more than 60% or more than 70% or more than 80%. Further preferably, an alkaline cook is performed in step (i) and 80% or more or 90% or more or 95% or more of the lignin initially present in the lignocellulosic biomass is present in the liquid SSL phase after step (ii).

In a preferred embodiment, since a (high yield) sulfite pretreatment step is being performed in step (i), the separation step (ii) results in 60% or more, preferably 75% or more, further preferably 90% or 95% or more of the cellulose that was initially present in the lignocellulosic biomass being present in the pulp phase.

Hydrolysis

According to step (iii) of the present process, the pulp as separated in step (ii) is hydrolyzed. The pulp is preferably hydrolyzed by enzymes or by microbial degradation, although a step of weak acid or strong acid hydrolysis may also be employed.

Cellulose is an insoluble linear polymer of repeating glucose (or more correctly cellobiose) units linked by β-1-

4-glucosidic bonds. In water, cellulose is hydrolyzed by attack of the electrophilic hydrogen of the water molecule on the glycosidic bond.

The rate of the reaction can be increased by use of elevated temperatures and pressures or can be catalyzed by dilute or concentrated acid or by enzymes.

Enzyme Hydrolysis

In cellulose chains each glucose unit has the potential to form three hydrogen bonds with monomers in adjacent chains, resulting in a stable crystalline structure resistant to hydrolysis.

According to a preferred embodiment of the present invention, extracellular or cell-membrane associated enzyme complexes (cellulases) that can specifically hydrolyze the cellulose polymer into soluble glucose monomers are used in the hydrolysis step (iii). Cellulases are multi-protein complexes consisting of synergistic enzymes with different specific activities that can be divided into exo- and endo-cellulases (glucanase) and β-glucosidase (cellobiase). In addition there are enzymes (hemicelluases, laccases, lignolytic peroxidases etc.) that can break down the other main components of lignocellulosic biomass. All these enzymes and any combination thereof are preferred enzymes that may be used in the enzymatic hydrolysis of step (iii).

Cellobiose is a known end-product inhibitor of glucanases and β-glucosidase is known to relieve this inhibition by converting cellobiose to glucose (rate-limiting step). In industrial processes, e.g. ethanol fermentation by yeast, cellulase saccharification efficiency can be improved by simultaneouos saccharification and fermentation (SSF). The biggest challenge with SSF is the different temperature optima for common hydrolytic enzymes and fermenting organisms. In addition to end-product inhibition, lignin is known to reduce enzyme performance by binding non-specifically to cellulases.

Both acid and enzyme hydrolysis of cellulose is limited by the strong crystalline nature of cellulose. The advantages of enzyme hydrolysis over acid hydrolysis are the use of mild conditions and minimal formation of degradation products, while disadvantages may be slow and expensive processing. Pretreatment of the cellulose is vital to increase the specific surface area of the cellulose and to reduce the crystallinity. Correct pretreatment has the advantages of increasing the enzyme hydrolysis rate due to more accessible substrate and also by removing potential inhibitory substances as noted above.

According to a preferred embodiment of the present invention, the hydrolysis step (iii) is an enzymatic hydrolysis step.

According to a preferred embodiment of the present invention, the enzymes are recycled, preferably by substrate adsorption and/or membrane separation.

Weak Acid Hydrolysis

Acid hydrolysis is a cheap and fast method for obtaining monosaccharides from cellulose and hemicellulose, but generates some degradation products. Severe acid hydrolysis conditions (high temperature or high acid concentration) degrade the monosaccharides to furfural and 5-hydroxymethylfurfural (HMF) and to aliphatic acids (such as AcOH, HCOOH and levulinic acid). However, weak acid hydrolysis may under certain circumstances be useful as a hydrolysis step.

A concentrated acid hydrolysis is preferably operated at temperatures from 20° C. to 100° C., and an acid strength in the range of 10% to 30%. Preferably sulfuric acid is used. The process requires corrosion resistant equipment and recovery of the acid.

Dilute acid hydrolysis is a simpler process, but needs higher temperatures (100° C. to 230° C.) and pressure. Different kinds of acids, with concentrations in the range of 0% to 5%, are preferably used (e.g. acetic acid, HCl or sulfuric acid). A dilute acid process will need pressure tolerant equipment.

In accordance with the present invention, a two step dilute acid hydrolysis process is particularly preferred.

Fermentation

Step (iv) of the present process relates to the fermentation of monosaccharides, in particular of hexoses and pentoses to ethanol or other sugar based chemicals or to produce biomass proteins.

Fermentation involves microorganisms that break down sugars releasing energy while the process results in products like an alcohol or an acid. *Saccharomyces cerevisiae* (Baker's yeast) is most frequently used to ferment hexoses to ethanol. One mole of glucose will stoichiometrically yield 2 moles of ethanol plus 2 moles of carbon dioxide. Bagasse pulp contains relatively large amounts of pentoses. These sugars can also be either fermented or metabolized to produce biomass proteins.

According to one embodiment of the present invention, bagasse is used as the raw material and fermentation step (iv) comprises the metabolizing of the hydrolysate of step (iii) into biomass proteins.

Lignosulfonate Processing

According to step (v) of the integrated process according to the present invention, the liquid SSL phase (a) from step (ii), i.e. the SSL comprising 50% or more or 60% or more or 70% or more or 80% or more of the lignin in the raw material, is processed to purified sulfonated lignin (lignosulfonates) and other products. The main step in the processing can be, for instance, fermentation, ultra filtration, sugar destruction, precipitation etc. Other steps may include drying, evaporation, stripping and neutralization etc.

Sulfonated lignin (lignosulfonates) can be used for a broad range of applications, including but not limited to chemicals, battery expanders, bypass protein, carbon black dispersions, cement, ceramics, concrete admixtures, emulsions, fertilizers, gypsum board, humic acid, industrial binders, industrial cleaners & water treatment additives, soil conditioners, micronutrients, mining and mineral processing, oil field chemicals, pelleting performance enhancers and road & soil dust control, among others.

Optional Further Delignification

In a preferred embodiment and with the object to further reduce the amount of lignin in the solid phase (pulp), an oxygen/alkali delignification step (extraction step) (i') may be part of the overall integrated process. This optional extraction step (i') is preferably performed after the pretreatment step (i) and before the separation step (ii).

Extracting more lignin has the advantage of increased lignosulfonate production.

Said additional delignification is preferably considered for pulps arising from the acid sulfite process since these pulps have comparatively high lignin contents. Oxygen delignification (10% NaOH charge, 6 bar oxygen) can give a 58 units (70 to 12) Kappa number reduction for an acid sulfite cooked pulp. The sulfonated lignin extracted during the delignification (approximately 25% of the sulfonated lignins extracted during the cook) has dispersing powers.

Lignin removing oxygen/alkali delignification is the preferred additional delignification step. During oxygen delignification, the pulp is subjected to oxygen pressure at high pH and elevated temperature.

EXAMPLES

The following applies in general throughout the entire specification and also for the claims:
"TS" denotes "Total Solids" and is the ratio between the weight of a sample after it has been dried at 105° C. for 16 h, and its original weight;
Temperature is given in ° C.
"w" denotes weight;
"%" denotes "weight %" if not specified otherwise;
"V/w" denotes "volume in mL" on weight in g if not specified otherwise.

Example 1

Alkaline Sulfite Cook, Enzymatic Hydrolysis

Bagasse [82% TS (Total Solids)] was used as feedstock. The feedstock was mixed with a cooking liquor consisting of 6% NaOH (w/w feed) and 24% $Na_2SO_3$ (w/w feed) with a liquid to solid ratio of 6 to 1.

The mixture was heated to 170° C. with a temperature increase of 1.6° C./min. The cook was kept at 170° C. for 60 min.

After the cook, i.e. after the pretreatment step according to the present invention, the solid (pulp, 51% of the TS) and the liquid (SSL, 49% of the TS) were separated by filtration. The pulp consisted of cellulose corresponding to 57% glucose, xylan corresponding to 24% xylose, 2% other carbohydrates, 5% lignin, 4% ash and 8% undefined components.

The SSL had a carbohydrate content of 11% (xylan corresponding to 6.4% xylose) on TS. The organic sulfur content in the SSL was 5.7% on TS. The remainder of the SSL was sulfonated lignin (lignosulfonate) and inorganic material. After evaporation, the SSL was tested for different applications and proved to be comparable to existing commercial products.

In the further process steps regarding the cellulose pulp, said pulp was enzymatically hydrolyzed with 0.7% (w protein/w feed) enzymes (0.5% cellulase, 0.05% β-glucosidase and 0.15% xylanase) at 50° C. for 48 hours. This resulted in a yield of 92% with respect to glucose and 90% with respect to xylose. The liquid (hydrolysate) was separated from the solid phase by centrifugation.

Example 2

Acid Sulfite Cook, Enzymatic Hydrolysis

Bagasse (82% TS) was used as feedstock. The feedstock was mixed with a cooking liquor with 35% $SO_2$ (w/w feed) and 3.1% hydroxide ion (w/w feed), NaOH was used as base. The liquid to solid ratio was 6 to 1. In said pretreatment step, the mixture was heated to 140° C. with a temperature increase of 1.9° C./min and a stop at 105° C. for 30 min. The cook was kept at 140° C. for 180 min.

After the cook, the solid (pulp, 45% of the TS) and liquid (SSL, 55% of the TS) phases were separated by filtration. The pulp consisted of cellulose, corresponding to 79% glucose, xylan, corresponding to 6% xylose, 1% other carbohydrates, 11% lignin, 3% ash.

The SSL had a carbohydrate content of 25% (19% xylose) on TS. The organic sulfur content in the SSL was 4.6% on TS. After evaporation, the SSL was tested for different applications and proved to be comparable to existing commercial products.

In the hydrolysis step after pretreatment, the pulp was enzymatically hydrolyzed with 0.55% (w protein/w feed) enzymes (0.5% cellulase, 0.05% β-glucosidase) at 50° C. for 48 hours. This resulted in a yield of 96% with respect to glucose and 75% with respect to xylose. The liquid (hydrolysate) was separated from the solid phase by centrifugation.

Example 3

Weak Alkaline Sulfite Cook, Enzymatic Hydrolysis

Bagasse (91.4% TS) was used as feedstock. The feedstock was mixed with a cooking liquor consisting of 6% $Na_2CO_3$ (w/w feed) and 16% $Na_2SO_3$ (w/w feed) with a liquid to solid ratio of 6 to 1.

The mixture was heated to 160° C. with a temperature increase of 1.3° C./min. The cook was kept at 160° C. for 180 min.

After the cook the solid (pulp, 53% of the TS) and the liquid (SSL, 47% of the TS) were separated by filtration. The pulp consisted of cellulose corresponding to 63% glucose, xylan corresponding to 27% xylose, 2% other carbohydrates, 5% lignin and 3% ash.

The SSL had a carbohydrate content of 7.5% (xylan corresponding to 4.7% xylose) on TS. The remainder of the SSL was sulfonated lignin (lignosulfonate) and inorganic material.

In the further steps of processing the cellulose pulp, said pulp was enzymatically hydrolyzed with two different substrate concentrations 5 and 10% w/w. Two different enzyme formulations were used for the saccharification, Novozymes Celluclast system, (5% "Celluclast 1.5 L", 0.5% β-glucosidase "Novozym 188" and 1% xylanase "Shearzyme" all in V/w pulp) and Genencors Accellerase 1500 system (24% V/w pulp) both formulations were tested at pH 5 (5 mM citrate buffer) incubated at 50° C. for 72 hours. Samples were taken at 6, 24, 48 and 72 hours. The results are provided in Table 1.

TABLE 1

Results of enzymatic hydrolysis weak alkaline cook, example 3.

| | Yield % | | | | | | | |
|---|---|---|---|---|---|---|---|---|
| | 6 h | | 24 h | | 48 h | | 72 h | |
| | Glucose | Xylose | Glucose | Xylose | Glucose | Xylose | Glucose | Xylose |
| Weak alkaline 5% Pulp concentration (Celluclast) | 22.1 | 31.0 | 50.3 | 63.3 | 71.4 | 90.0 | 81.0 | 90.0 |
| Weak alkaline 5% Pulp concentration (Accellerase) | 35.3 | 52.2 | 56.8 | 53.8 | 61.5 | 58.7 | 69.5 | 65.2 |
| Weak alkaline 10% Pulp concentration (Celluclast) | 13.9 | 24.6 | 38.4 | 57.1 | 61.0 | 76.3 | 67.0 | 76.3 |
| Weak alkaline 10% Pulp concentration (Accellerase) | 22.1 | 22.8 | 44.8 | 49.9 | 49.4 | 48.9 | 54.7 | 57.9 |

Example 4

Acid Sulfite Cook II, Enzymatic Hydrolysis

Bagasse (91.4% TS) was used as feedstock. The feedstock was mixed with a cooking liquor with 47% $SO_2$ (w/w feed) and 3.8% hydroxide ion (w/w feed). NaOH was used as base. The liquid solid ratio was 6 to 1. In said pretreatment step, the mixture was heated to 140° C. with a temperature increase of 1.5° C./min. The cook was kept at 140° C. for 120 min.

After the cook, the solid (pulp, 47% of the TS) and liquid (SSL, 53% of the TS) phases were separated by filtration. The pulp consisted of cellulose corresponding to 79% glucose, xylan corresponding to 8% xylose, less then 1% other carbohydrates, 11% lignin and 2% ash.

The SSL had a carbohydrate content of 22.8% (20.2% xylose) based on TS. The organic sulfur content in the SSL was 4.6% based on TS.

In the further process steps regarding the cellulose pulp, said pulp was enzymatically hydrolyzed with two different substrate concentrations 5 and 10% w/w. Two different enzyme formulations were used for the saccharification, Novozymes Celluclast system, (5% "Celluclast 1.5 L", 0.5% β-glucosidase "Novozym 188" and 1% xylanase "Shearzyme" all in V/w pulp) and Genencors Accellerase 1500 system (24% V/w pulp) both formulations were tested at pH 5 (5 mM citrate buffer) incubated in 50° C. for 72 hours. Samples were taken at 6, 24, 48 and 72 hours. The results are provided in Table 2 and show that the process of the invention works well with different types of enzymes.

TABLE 2

Results enzymatic hydrolysis acid cook II, example 4.

| | Yield % | | | | | | | |
|---|---|---|---|---|---|---|---|---|
| | 6 h | | 24 h | | 48 h | | 72 h | |
| | Glucose | Xylose | Glucose | Xylose | Glucose | Xylose | Glucose | Xylose |
| Acid 5% Pulp concentration (Celluclast) | 21.9 | 33.3 | 46.0 | 52.6 | 61.7 | 66.3 | 61.7 | 66.3 |
| Acid 5% Pulp concentration (Accellerase) | 33.3 | 34.6 | 48.7 | 52.4 | 50.5 | 57.2 | 57.8 | 66.3 |
| Acid 10% Pulp concentration (Celluclast) | 17.0 | 26.8 | 40.0 | 50.8 | 49.8 | 54.2 | 49.7 | 56.5 |
| Acid 10% Pulp concentration (Accellerase) | 23.5 | 24.8 | 48.2 | 48.5 | 51.3 | 54.2 | 54.7 | 58.8 |

Example 5

Weak Alkaline and Acid Sulfite Cooking of Straw, Enzymatic Hydrolysis

Norwegian straw (92.5% TS) was used as feedstock. The feedstock was divided in two parts. Part one was mixed with a cooking liquor consisting of 16% $Na_2SO_3$ (w/w feed) and 6% $Na_2CO_3$ (w/w feed). In said pretreatment step, the mixture was heated to 160° C. with a temperature increase of 2° C./min. The cook was kept at 160° C. for 120 min.

Part two was mixed with a cooking liquor with 36.1% $SO_2$ (w/w feed) and 3.8% hydroxide ion (w/w feed), NaOH was used as base. In said pretreatment step, the mixture was heated to 132° C. with a temperature increase of 1.8° C./min. The cook was kept at 132° C. for 180 min.

The liquid to solid ratio was 6:1 for both cooks.

After the cook (weak alkaline/acid), the solid (pulp, 49/45% of the TS) and liquid (SSL, 51/55% of the TS) phases were separated by filtration (only the dry solids were taken into account determining the percentages). The pulp consisted of cellulose corresponding to 63/81% glucose, xylan corresponding to 25/10% xylose, 2/less then 1% other carbohydrates, 7/15% lignin and 2/0% undefined components.

The SSL had a carbohydrate content of 14.3/21.1% (xylan corresponding to 8.5% xylose/16.7% xylose) on TS.

In the further process steps regarding the cellulose pulp, said pulp was enzymatically hydrolyzed at a substrate concentration of 8% w/w. One enzyme formulation, Novozymes Celluclast system, (10% "Celluclast 1.5 L", 15% β-glucosidase "Novozym 188" and 2% xylanase "Shearzyme" all in V/w pulp) were tested at pH 5 (5 mM citrate buffer) incubated in 50° C. for 24 hours. Samples were taken after 24 hours. The use of the weak alkaline cooked sample resulted in a yield of 62% glucose and 68% xylose. The use of the acid cooked sample resulted in a yield of 60% glucose and 78% xylose.

Example 6

Acid, Weak Alkaline and Alkaline Sulfite Cooking of Bagasse, Enzymatic Hydrolysis A set of 25 acid, weak alkaline and alkaline cooks were conducted, bagasse (65% TS) was used as feedstock. Conditions covering a broad range were tested. Acid cooks: 20-50% $SO_2$ (w/w feed) and 2-8% hydroxide ion (w/w feed), NaOH was used as base. The cooking temperature varied from 125-160° C. and time from 60-180 min. Weak alkaline cooks: $Na_2SO_3$ 10-40% (w/w feed) and $Na_2CO_3$ 5-25% (w/w feed). The cooking temperature varied from 140-180° C. and cooking time from 60-180 min. Alkaline cooks: $Na_2SO_3$ 10-40% (w/w feed) and NaOH 5-30% (w/w feed). The cooking temperature varied from 140-180° C. and time from 60-180 min.

The cooks resulted in 25 different pulps with a varying amount of residual lignin 1.6-51% (Kappa number 8-102)

Figure 3:
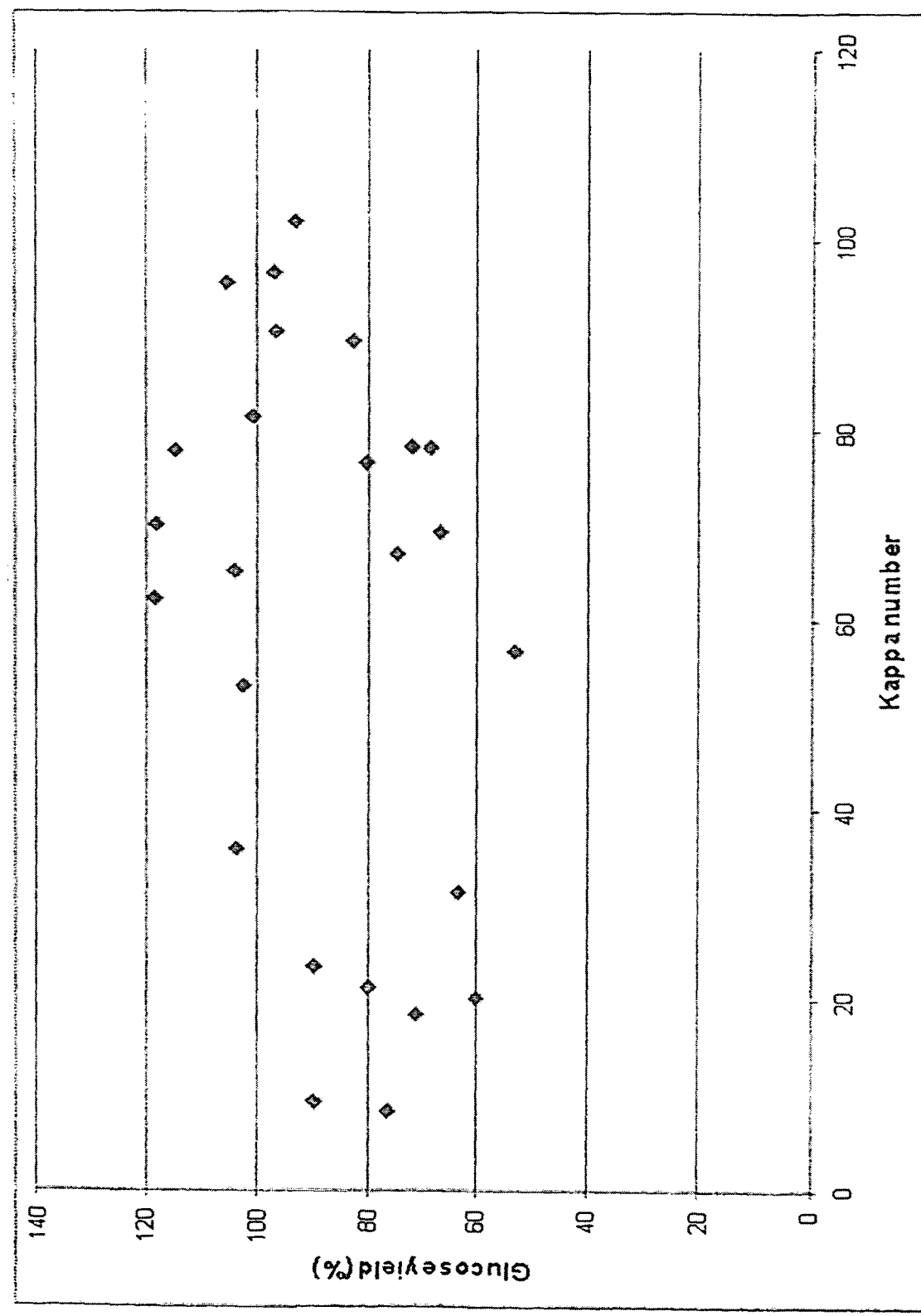
FIG. 3 shows results of enzymatic hydrolysis of the soda cooks I and II of comparative Example I [correlation between Kappa number (residual lignin) and glucose yield (digestability)].

In the further process steps regarding the pulp, said pulp was enzymatically hydrolyzed at a substrate concentration of 2% w/w. One enzyme formulation, Novozymes Celluclast system, (5% "Celluclast 1.5 L", 0.5% β-glucosidase "Novozym 188" and 1% xylanase "Shearzyme" all in V/w pulp) were tested at pH 5 (5 mM citrate buffer) incubated at 50° C. for 48 hours. Glucose yield as a plot of Kappa number (residual lignin) is presented in FIG. 3. The results in FIG. 3 show that there is no clear correlation between the digestabilities of the pulps and their lignin contents (Kappa numbers). In other words, despite the fact that the residual content varies significantly from low to high, this has no noticeable effect on the yield, which varies between 60% and 100% (values >100% are due to the error bar) without any correlation with Kappa. This is believed to be due to the "deactivation" of lignin by the sulfite process as described above.

Example 7

Ethanol Fermentation

Fermentation was performed using Baker's yeast (Saccharomyces cerevisiae) in 2 L Biostat B plus fermentors (Sartorius Stedium) as batch cultures under controlled conditions.

Agar plates with YPD [yeast extract (10 g/l), peptone (20 g/L), dextrose (20 g/L), agar (20 g/L)] were used to maintain the strain. A single colony was picked and initially inoculated into 100 ml YPD media and incubated overnight at 34° C. and 200 rpm. The culture was cryopreserved in 30% glycerol at −80° C. in 10 ml aliquots. A thawed aliquot was used as inoculum for a starter culture that was grown in 600 ml YPD medium overnight. The cells were harvested by centrifugation, washed with sodium chloride solution (9 g/L) and centrifuged.

Hydrolysates prepared according to the procedures of Examples 3 and 4 above were amended with nutrient solution [$(NH_4)_2SO_4$ (0.44 g/L), $KH_2PO_4$ (2.0 g/L) and $MgSO_4$ (0.50 mg/L)] and 1.0 g/L of yeast extract and pH was adjusted to 4.6. An inoculum pellet (adjusted to give an initial biomass concentration of ~2 g $l^{-1}$ dry weight) was suspended therein. The glucose level during the fermentation was monitored by using a glucometer (Glucometer Elite, Bayer AG, Germany). Samples taken from the fermentors were centrifuged at 13000 g for 1 min. The supernatant was filtered through a HPLC filter (0.45 μm GHP Acrodisc 13 mm syringe filter) and analyzed for glucose content (ion chromatography) and ethanol concentration (gas chromatography).

The hydrolysates obtained by using the procedures in Examples 3 and 4 both gave a yield coefficient of 0.50 (g ethanol/g glucose).

COMPARATIVE EXAMPLES

Comparative Example I

Soda Cooks, Enzymatic Hydrolysis

Bagasse (91.4% TS) was used as feedstock. The feedstock was mixed with cooking liquor consisting of 16% NaOH (w/w feed) with a liquid to solid ratio of 6 to 1.

Soda Cook I:

The mixture was heated to 160° C. with a temperature increase of 1.3° C./min. The cook was kept at 160° C. for 180 min.

Soda Cook II:

The mixture was heated to 140° C. with a temperature increase of 1.5° C./min. The cook was kept at 140° C. for 120 min.

After the cook, the solid (pulp, 48/52% of the TS) and liquid (black liquor, 52/48% of the TS) were separated by filtration (only the dry solids are taken into account determining the percentages). The pulp consisted of cellulose corresponding to 68/65% glucose, xylan corresponding to 26/26% xylose, 2/2% other carbohydrates, 4/5% lignin, 2/2% ash.

The SSL had a carbohydrate content of 9.6/9.2% (5.7/5.9% xylose) on dry substance. The remainder of the black liquor was degraded lignin, aliphatic acids and inorganic substances.

In the further process steps regarding the cellulose pulp, said pulp was enzymatically hydrolyzed with two different substrate concentrations 5 and 10% w/w. Novozymes Celluclast system, (5% "Celluclast 1.5 L", 0.5% β-glucosidase "Novozym 188" and 1% xylanase "Shearzyme" all in V/w pulp) was tested at pH 5 (5 mM citrate buffer) incubated in 50° C. for 72 hours. Samples were taken at 6, 24, 48 and 72 hours, results are shown in Table 3.

TABLE 3

Results of enzymatic hydrolysis of soda cook I and II, Comparative Example I.

| | Yield % | | | | | | | |
|---|---|---|---|---|---|---|---|---|
| | 6 h | | 24 h | | 48 h | | 72 h | |
| | Glucose | Xylose | Glucose | Xylose | Glucose | Xylose | Glucose | Xylose |
| Soda I 5% Pulp concentration | 12.8 | 19.8 | 29.4 | 43.0 | 48.0 | 61.8 | 48.3 | 62.4 |
| Soda I 10% Pulp concentration | 4.3 | 11.3 | 12.7 | 34.4 | 26.4 | 60.1 | 47.1 | 61.6 |
| Soda II 5% Pulp concentration | 12.9 | 19.7 | 28.9 | 43.2 | 46.9 | 60.9 | 54.8 | 63.9 |
| Soda II 10% Pulp concentration | 6.5 | 12.2 | 10.7 | 33.6 | 21.5 | 57.4 | 30.1 | 54.2 |

Interpretation of Comparative Example I and Examples 3 and 4

Figure 4:
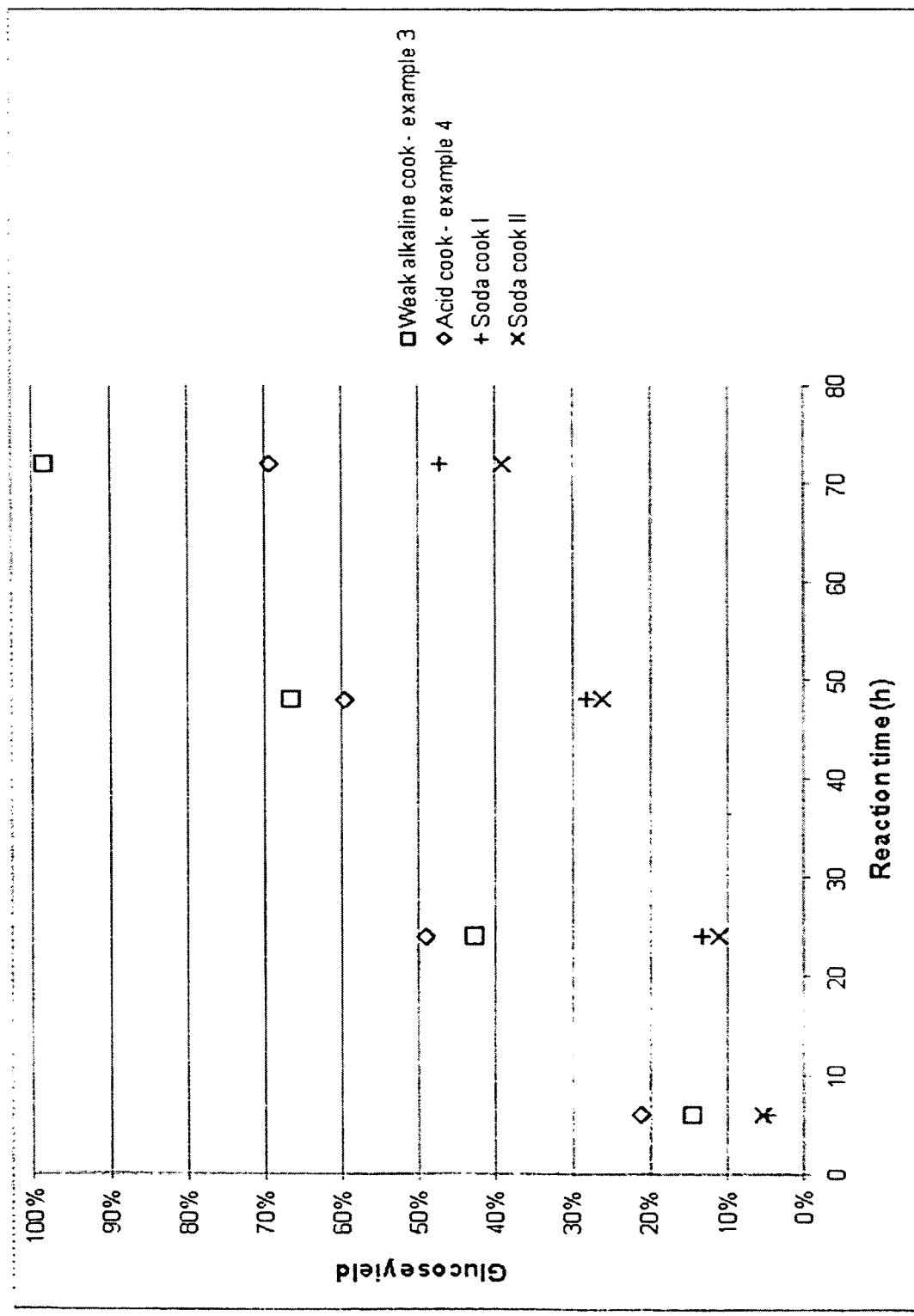
FIG. 4 shows the comparison of sulfite treatment and soda cooking pulps during enzymatic hydrolysis with Celluclast.

When the pretreatment method of the present invention is compared with a conventional soda cook, several differences can be observed. The claimed process generates a liquid fraction (SSL) which easily can be transformed into products with extensive dispersing properties. When the second step (hydrolysis/saccharification) of the process is examined, a clear difference exists in digestibility between soda and sulfite cooked samples, see FIG. 4.

It can clearly be seen that the sulfite pretreated bagasse is much easier to hydrolyze then the soda cooked bagasse. Prior to the present invention, the prejudice in the art was that there is a direct correlation between enzymatic digestibility and the amount of lignin for the pretreated materials (see, for example: Mooney C. A. et al., 1998, "The effect of the initial pore volume and lignin content on the enzymatic hydrolysis of softwood", Biores. Technol. 64, 2, 113-119, and Lu Y. et al., 2002, "Cellulase adsorption and an evaluation of enzyme recycle during hydrolysis of steam-exploded softwood residues", Appl. Biochem. Biotechnol. 98-100, 641-654.). The sulfite pretreatment results in more easily hydrolyzed pulps than the soda cooks, despite the fact that the lignin content is lower in the soda cooks. This finding strongly indicates that the lignin content is not a rate determining factor for the hydrolysis of sulfite pretreated material. This has previously not been seen for delignifying pretreatments and was not anticipated.

The invention claimed is:

1. Process for producing monosaccharides, sugar based chemicals, biofuels or materials together with sulfonated lignin from a lignocellulosic biomass comprising at least the following steps:

providing a lignocellulosic biomass;

pretreating the lignocellulosic biomass, comprising:

sulfite cooking at a temperature of not greater than 180° C., wherein the sulfite cooking comprises an acid cook comprising an amount of $SO_2$ from 30 to 50% w/w, and an amount of base from 1 to 10% w/w; and dissolving the lignocellulosic biomass into a liquid "spent sulfite liquor" phase and a pulp phase;

separating 60% or more of a sulfonated lignin from the pretreated lignocellulosic biomass into at least the liquid "spent sulfite liquor" phase;

separating 70% or more of a cellulose from the pretreated lignocellulosic biomass into at least and the pulp phase;

enzymatically hydrolyzing the pulp phase into a sugar chemistry platform comprising monosaccharides; and directly converting and/or further processing the sulfonated lignin of the liquid "spent sulfite liquor" phase into useful chemicals and/or materials.

2. Process according to claim 1, wherein the monosaccharides comprise hexoses and pentoses.

3. Process according to claim 2, wherein the hexoses and pentoses comprise xylose and glucose.

4. Process according to claim 1, wherein the lignocellulosic biomass comprises wood, annual plants, agricultural residues or waste, in particular bagasse or energy crops, wherein when bagasse is used as the raw material and the step of further processing the sugar chemistry platform comprising monosaccharides into useful chemicals, biofuels and/or proteins comprises the step of metabolizing the hydrolysate into biofuels, or wherein bagasse is used as the raw material and the step of further processing the sugar chemistry platform comprising monosaccharides into useful chemicals, biofuels and/or proteins comprises metabolizing the hydrolysate into biomass proteins.

5. Process according to claim 4, wherein the lignocellulosic biomass used in the process does not require mechanical (pre)treatment and wherein the step of sulfite cooking is the only chemical pretreatment prior to hydrolysis.

6. Process according to claim 1, wherein an organic part of the liquid "spent sulfite liquor" phase predominantly comprises lignin in the form of sulfonated lignin, i.e. comprises more than 60% of the lignin initially present in the lignocellulosic biomass.

7. Process according to claim 1, wherein 80% or more of the cellulose that was initially present in the lignocellulosic biomass is present in the pulp.

8. Process according to claim 1, wherein the step of sulfite cooking is performed as the only pretreatment, wherein 70% or more of the overall hemicellulose from the lignocellulosic biomass is hydrolyzed to monosaccharides.

9. Process according to claim 8, wherein the temperature is in the range from 125° C. to 160° C.

10. Process according to claim 1, wherein the base is selected from the group consisting of NaOH, $Ca(OH)_2$, $Mg(OH)_2$ and $NH_4OH$.

11. Process according to claim 10, wherein the cook is performed for a time interval of 60 to 300 minutes.

12. Process according to claim 1, wherein the step of enzymatically hydrolyzing comprises employing extracellular or cell-membrane associated enzyme complexes, in particular mixture of cellulases and β-glucosidases, that can specifically hydrolyze the cellulose polymer into monosaccharides such as soluble glucose monomers wherein the enzymes are optionally recycled.

13. Process according to claim 12, wherein the enzymes comprise cellulases, hemicellulases and β-glucosidases.

14. Process according to claim 1, further comprising after the pretreating step and before the separating step, step of an oxygen/alkali delignification.

15. Process according to claim 1, wherein an organic part of the liquid "spent sulfite liquor" phase predominantly comprises lignin in the form of sulfonated lignin, i.e. comprises more than 70% of the lignin initially present in the lignocellulosic biomass.

16. Process according to claim 1, wherein an organic part of the liquid "spent sulfite liquor" phase predominantly comprises lignin in the form of sulfonated lignin, i.e. comprises more than 80% of the lignin initially present in the lignocellulosic biomass.

17. Process according to claim 1, further comprising the step of processing the sugar chemistry platform comprising monosaccharides into useful chemicals, biofuels and/or proteins.

* * * * *